(12) United States Patent
Morse et al.

(10) Patent No.: US 7,201,039 B2
(45) Date of Patent: Apr. 10, 2007

(54) AXIAL FLOW SCAN TESTABLE FILTER SYSTEM

(75) Inventors: Thomas C. Morse, Greenville, NC (US); Mark Huza, Columbia, MD (US)

(73) Assignee: Camfil Farr, Inc., Rancho Dominguez, CA (US)

( * ) Notice: Subject to any disclaimer, the term of this patent is extended or adjusted under 35 U.S.C. 154(b) by 0 days.

(21) Appl. No.: 11/225,812

(22) Filed: Sep. 13, 2005

(65) Prior Publication Data
US 2006/0053864 A1    Mar. 16, 2006

Related U.S. Application Data

(60) Provisional application No. 60/609,684, filed on Sep. 13, 2004.

(51) Int. Cl.
*G01N 15/08* (2006.01)
(52) U.S. Cl. .................. 73/38; 73/863.56; 73/40.7
(58) Field of Classification Search ............. 73/23.2, 73/38, 863.56, 40.7
See application file for complete search history.

(56) References Cited

U.S. PATENT DOCUMENTS

RE27,701 E * 7/1973 Allen, Jr. et al. ............ 55/500
4,197,098 A * 4/1980 Stiehl et al. .................. 96/110
4,324,568 A * 4/1982 Wilcox et al. ................ 95/286
4,494,403 A * 1/1985 Bowers et al. .............. 73/40.7

FOREIGN PATENT DOCUMENTS

JP      59-010831 A      1/1984
JP      59010831 A  *   1/1984

OTHER PUBLICATIONS

International Search Report for PCT/US2005/032519.

* cited by examiner

*Primary Examiner*—Hezron Williams
*Assistant Examiner*—Samir M. Shah
(74) *Attorney, Agent, or Firm*—Keith Taboada, Esq.; Patterson & Sheridan, LLP

(57) ABSTRACT

A filter system having in-situ scan capabilities is provided. In one embodiment of the invention, the system includes a downstream probe which may be rotated to scan the field of a filter installed in the system. The probe may be utilized for leak detection, velocity measurements, efficiency testing and the like. In one embodiment, one or more probes are rotated downstream of the filter to scan the downstream face of the filter.

21 Claims, 14 Drawing Sheets

FIG. 8

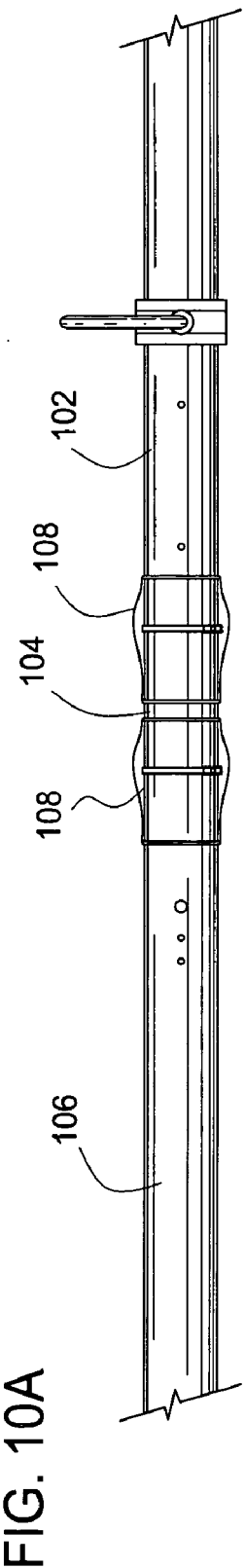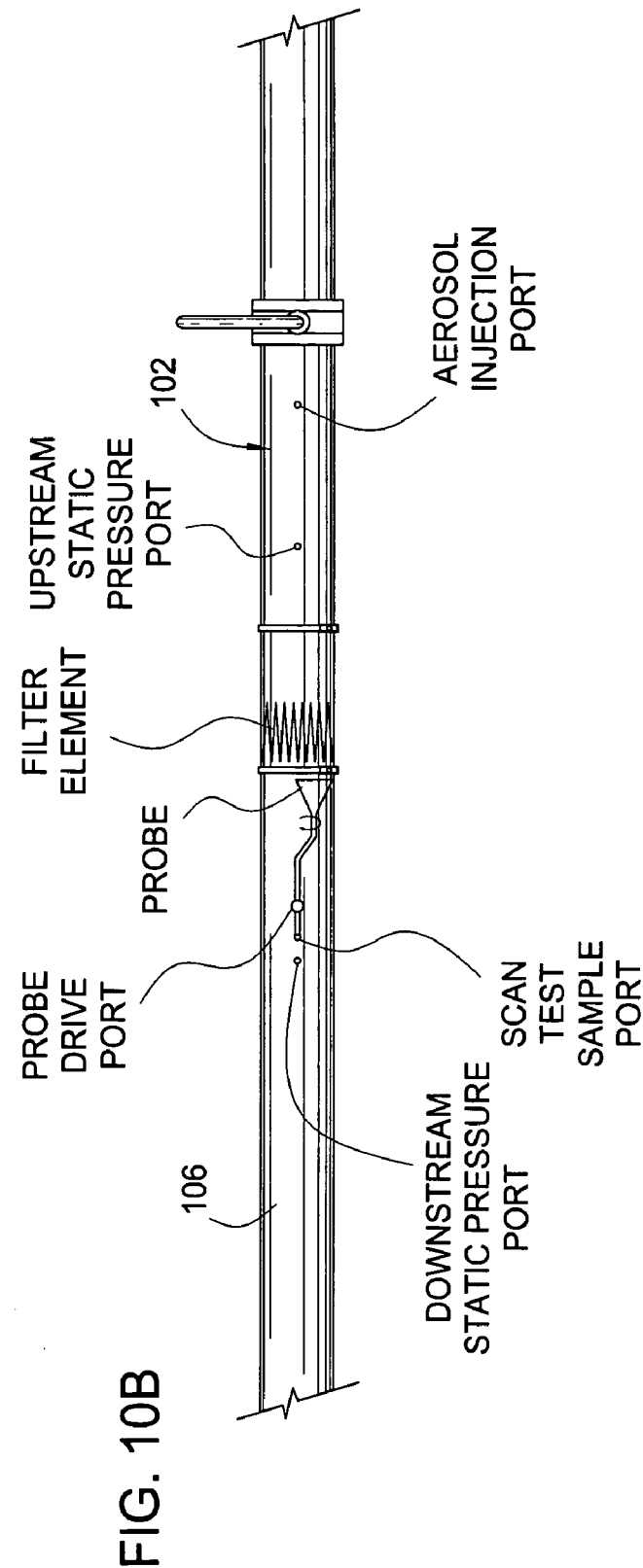
FIG. 10A
FIG. 10B

AEROSOL INJECTION PORT
UPSTREAM STATIC PRESSURE PORT
FILTER ELEMENT
PROBE
PROBE DRIVE PORT
SCAN TEST SAMPLE PORT
DOWNSTREAM STATIC PRESSURE PORT

AXIAL FLOW SCAN TESTABLE FILTER SYSTEM

RELATED APPLICATIONS

The application claims benefit from U.S. Provisional Patent Application No. 60/609,684, filed Sep. 13, 2004 by Thomas C. Morse, which is incorporated by reference in its entirety.

FIELD OF INVENTION

The invention generally relates to a filtration system having filter scanning capability.

BACKGROUND OF THE INVENTION

Conventional scan test systems for high efficiency air filters are designed for manual in-situ scanning of square filters. In some applications, the amount of available space is limited, and/or the cost of conventional scan test systems are financially prohibitive.

Therefore, there is a need for an improved filter system with in-situ filter testing.

SUMMARY OF THE INVENTION

A filter system having in situ scan capabilities is provided. In one embodiment of the invention, the system includes a downstream probe which may be rotated to scan the field of a filter installed in the system. The probe may be utilized for leak detection, velocity measurements, efficiency testing and the like. In one embodiment, one or more probes are rotated downstream of the filter to scan the downstream face of the filter.

BRIEF DESCRIPTION OF THE DRAWINGS

So that the manner in which the above recited features of the present invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIGS. 8–9 depict the exterior of the scan housing illustrating penetrations; and FIGS. 10A–D depict schematic side views of some alternative embodiments of scan testable filter system.

To facilitate understanding, identical reference numerals have been used, wherever possible, to designate identical elements that are common to the figures. It is contemplated that elements of one embodiment may be beneficially incorporated in other embodiments with out further recitation.

DETAILED DESCRIPTION

Figure 1:
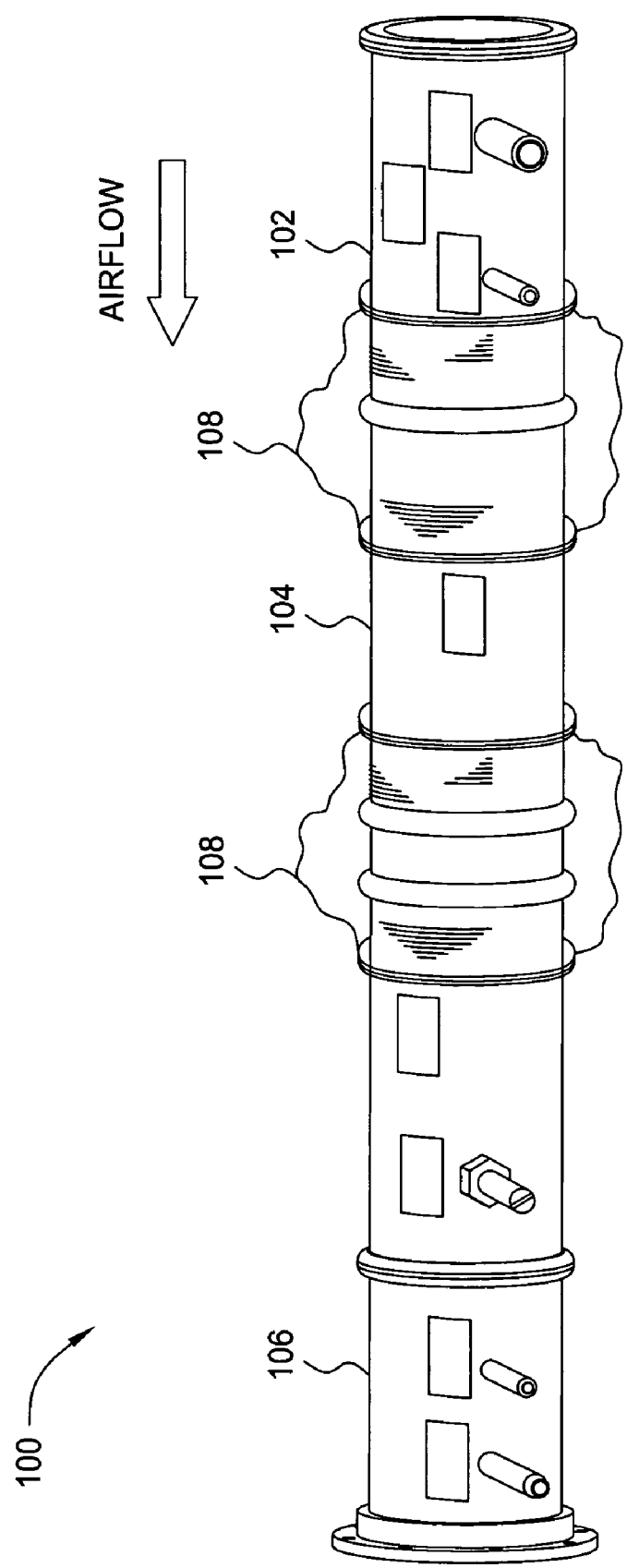
FIG. 1 depicts a side view of one embodiment of a scan testable filter system of the present invention.

FIG. 1 depicts one embodiment of a scan testable axial flow filter containment system 100. The system 100 generally includes an upstream duct work housing 102, a filter housing 104 and a scan test housing 106. The upstream duct work housing 102, the filter housing 104 and the scan test housing 106 form a pressure boundary of the system 100. The upstream duct work housing 102 and the scan test housing 106 are generally coupled to the facilities duct work.

A filter element is replaceably disposed in, or permanently coupled to, the filter housing 104 in a manner that causes air, flowing from the upstream duct work housing 102 to the scan test housing 106, to be filtered. Although the axial flow filter system 100 is shown having a circular filter housing 104, the system may be adapted to utilize filters and/or filter housings having other geometric configurations. In one embodiment, the filter element has a pleat orientation perpendicular to the direction of air flow, as shown in FIG. 10B.

The system 100 may be equipped with PVC bags 108 for bag-in, bag-out replacement of the filter housing 104, as depicted in FIG. 1, FIGS. 3A–E, FIGS. 10A and 10C, among other Figures. FIG. 10B depicts the ports associated with the different housings of the system, and include an upstream static port and an aerosol injection port disposed through the upstream duct work housing 102, and downstream static port and sample port disposed through the scan test housing 106. The ports are disposed through the housings 102, 106 in a manner that prevents unintended leakage therethrough, for example, by welding or caulking. The upstream duct work housing 102 and scan test housing 106 may also include decontamination ports 1002 as seen in FIGS. 10C–D.

Figure 2:
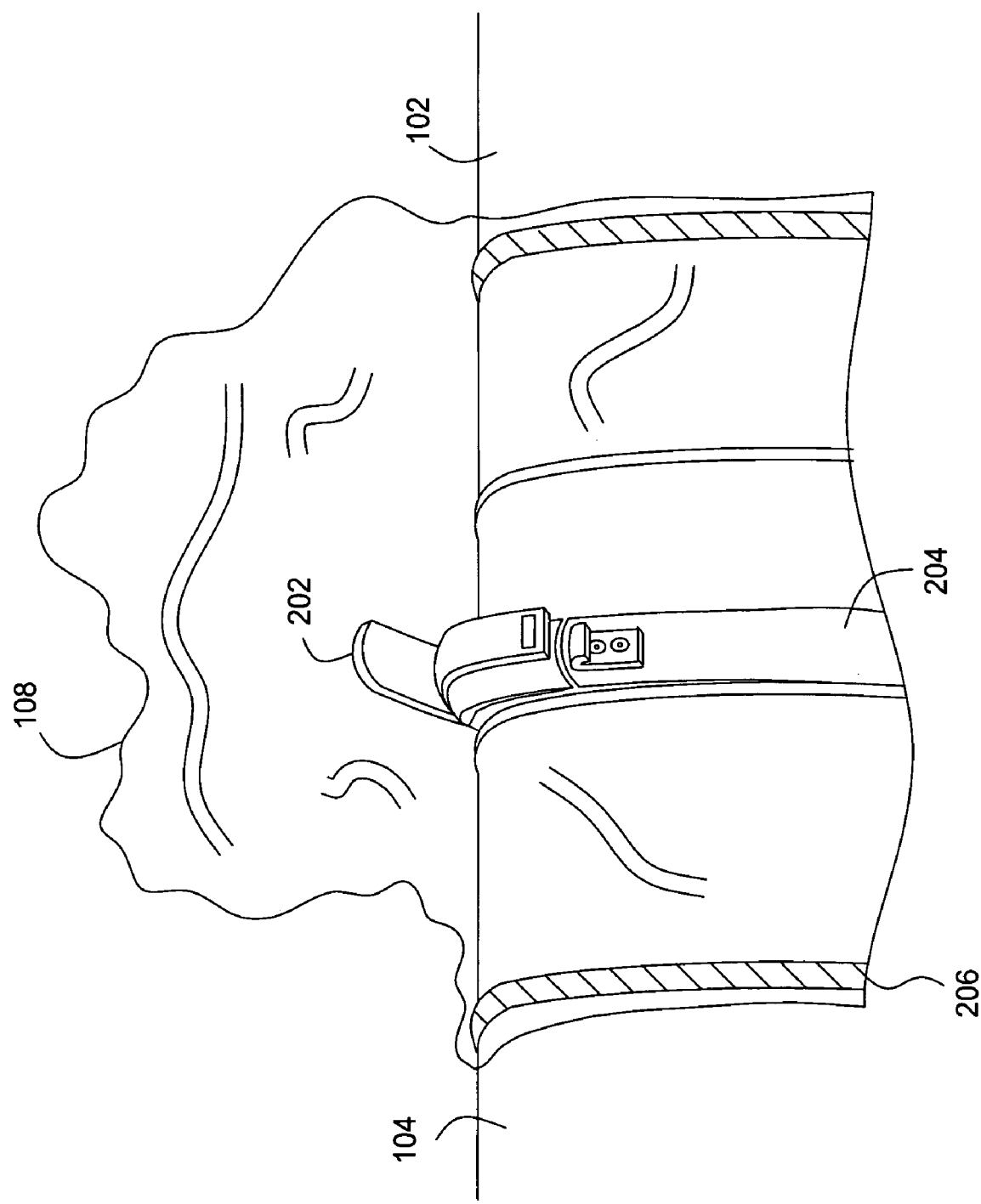
FIG. 2 depicts a partial view of the filter system of FIG. 1 illustrating a latch operated through a containment bag.
Figure 3A:
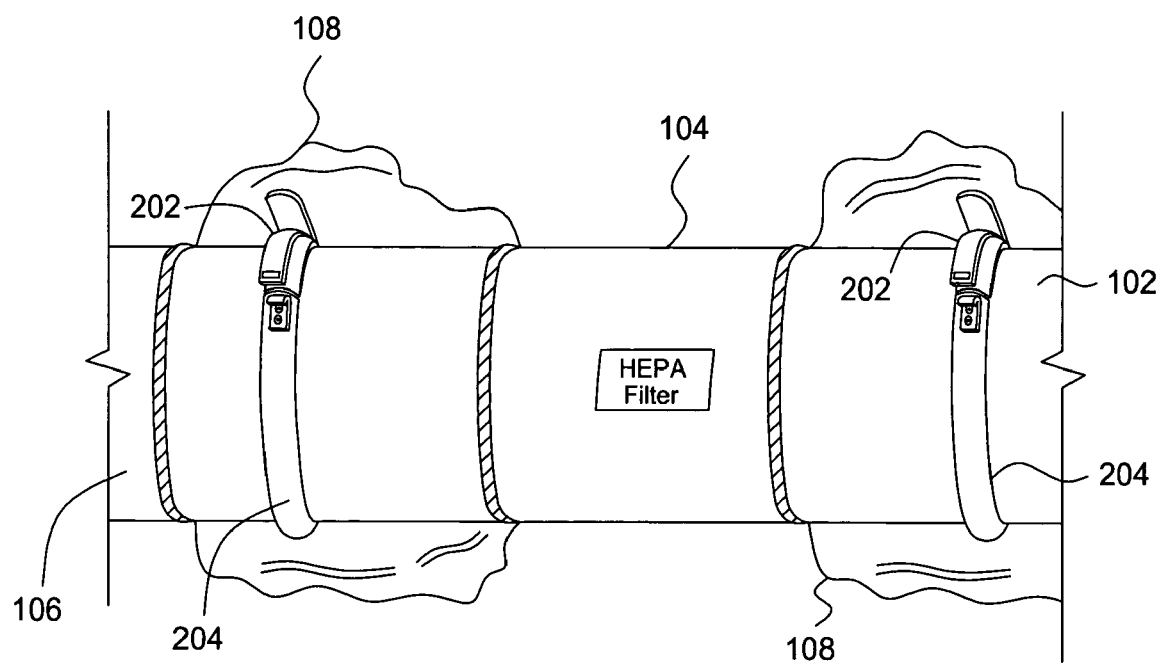
FIGS. 3A–3E depict a filter housing being removed from the filter system.
Figure 3B:
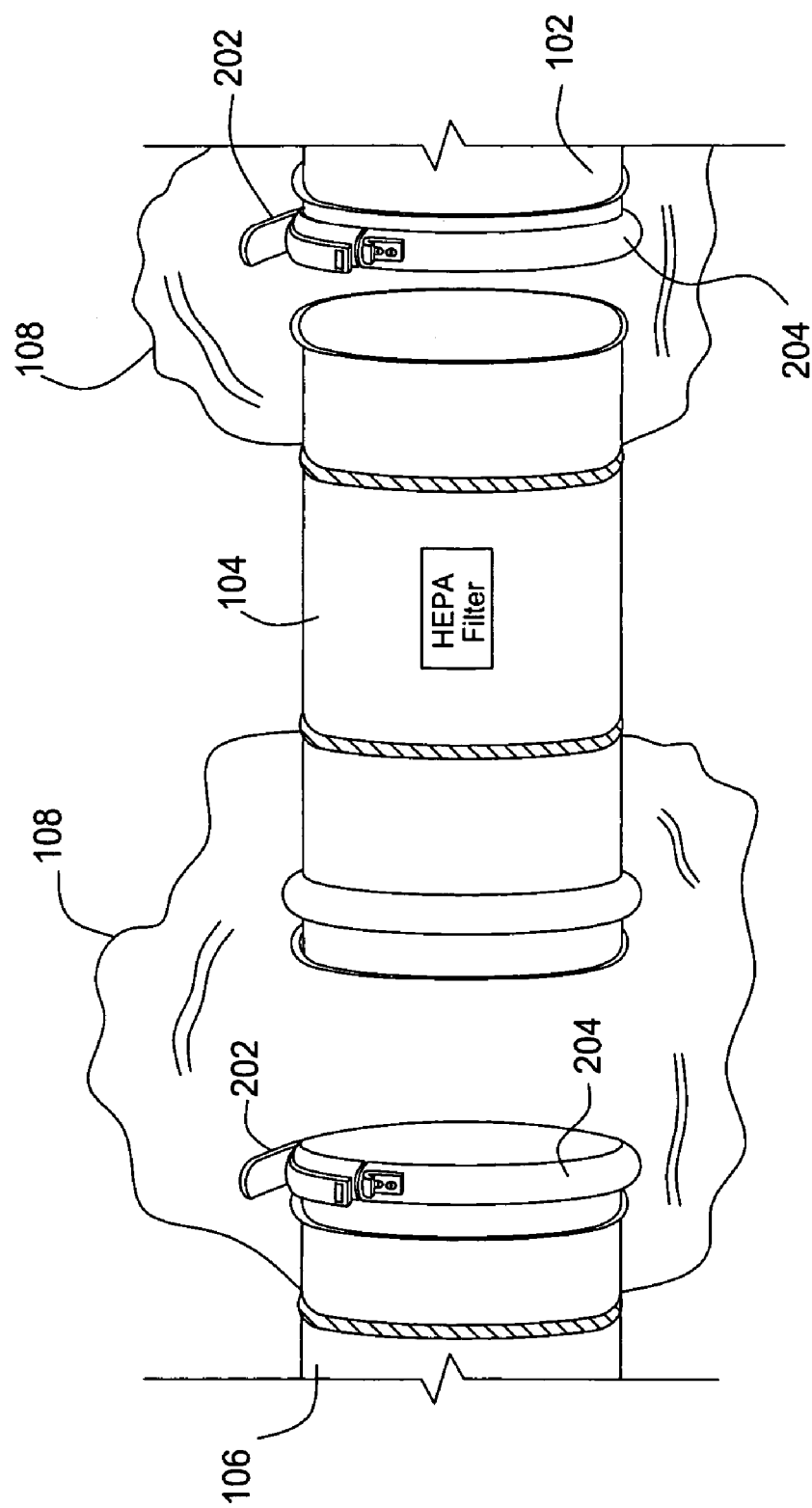
Figure 3C:
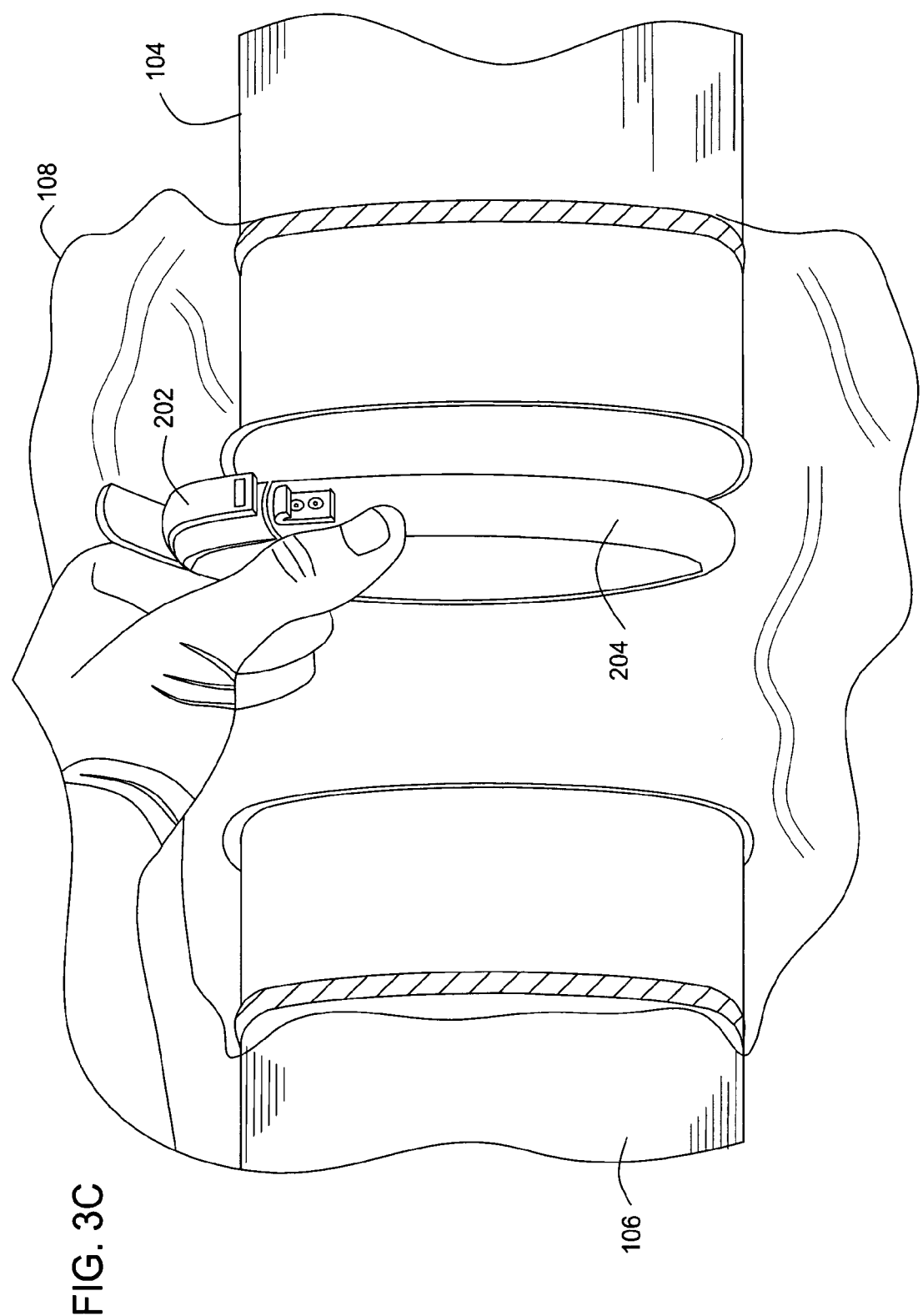
Figure 3D:
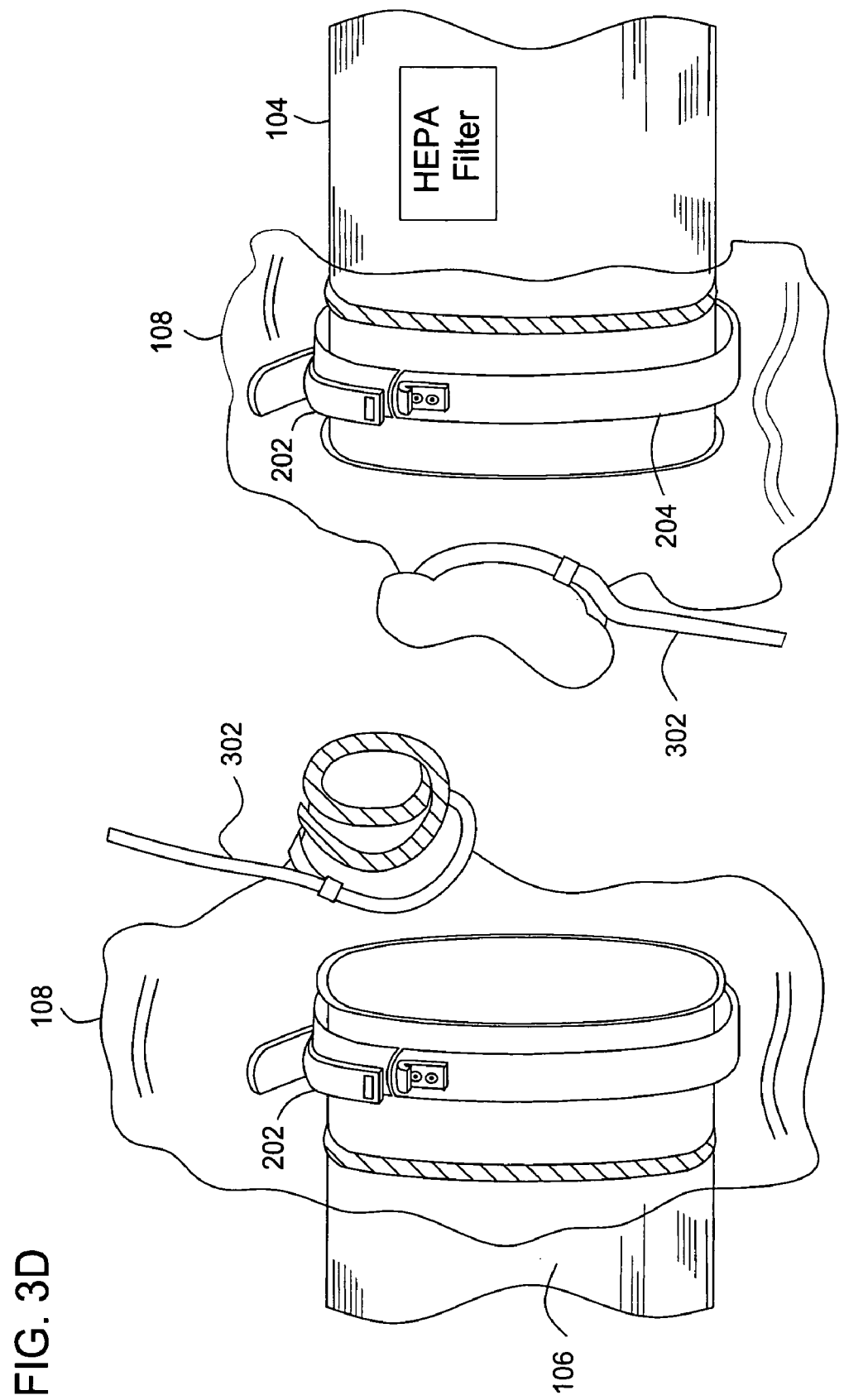
Figure 3E:
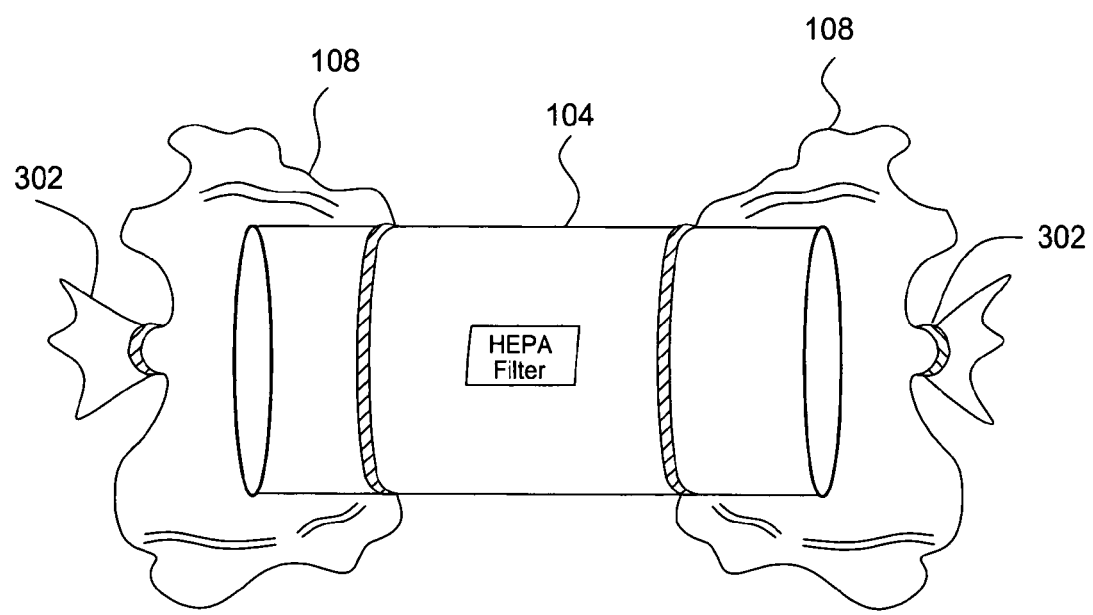

The housings 102, 104 and 106 are secured together in a manner that prevents leakage while allowing the filter housing 104 to be easily removed for filter replacement. In one embodiment, a band 204 and latch 202 are utilized for securing the housings 102, 104 and 106. The latch 202 (shown coupling the housings 102 and 104 in FIG. 2) may be operated through the bag 108.

FIGS. 3A–E depict the filter housing 104 being removed from the system 100. First, latches 202 are unlocked and the bands 204 released to separate the filter housing 104 from the housings 102 and 106. While the bag 108 remains sealed to the housings 106 and 104, the bag 108 is gathered between the housings and banded using a tie 302 or other suitable item. The bag 108 is cut between the bands (e.g., ties 302) to isolate one end of the filter housing 104. The other end of the filter housing 104 mating with the housing 102 is similarly sealed so that the used filter housing 104 (and/or filter element) may be disposed without contaminating the environment or technicians.

Figure 4:
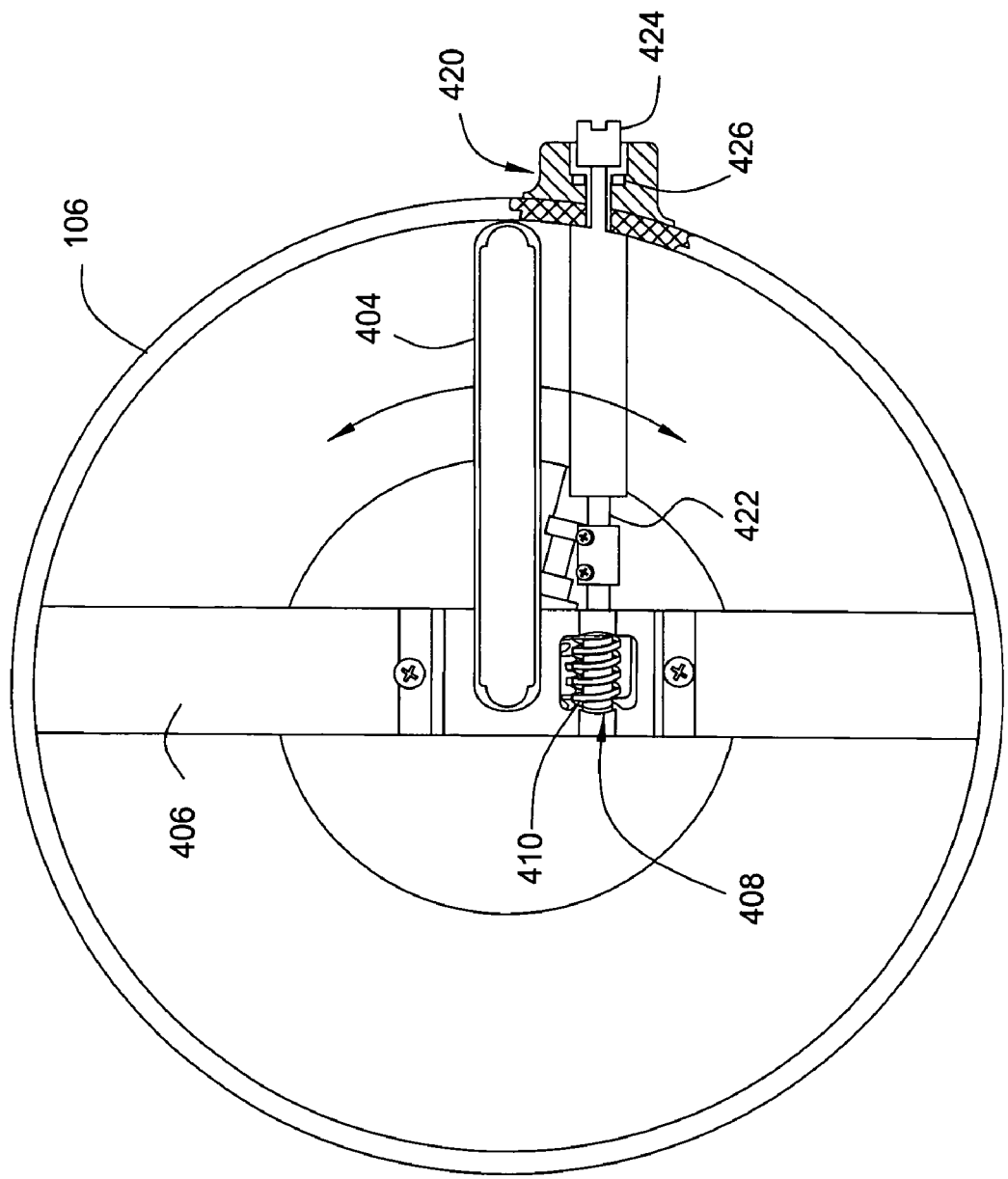
FIG. 4 is an interior view of the scan housing of the filter system of FIG. 1.

FIG. 4 is an end view (looking downstream) of the scan housing 106 illustrating the probe 402. The probe 402 is rotationally coupled to a bracket 406 that is coupled to the scan housing 106. An actuator 408 is configured to rotate the probe 402 within the scan housing 106 so that the probe 402 scans the face of the filter disposed in the filter housing 104. It is contemplated that one or more probes may be utilized, and each probe may have a length approximately equal to, or less than the inside diameter of the scan housing 106. Generally, the number, size and geometry of the probe 402 is selected to provide good test results for a predefined test criteria, for example, as suggested by IEST or other organization. In the embodiment depicted in FIG. 4, the probe 402 is approximately equal to ½ the inside diameter of the housing 106. This allows the probe 402 to extend from the centerline of the scan housing 106 to the inside diameter of the scan housing 106, so that as the probe 402 is rotated, the probe 402 covers the sectional area within the scan housing 106 (and thus, the face of the filter element) with an overlapping motion to ensure complete sampling across the face of the filter. Other probe(s) configurations are contemplated that allow the entire filter face (or duct sectional area) to be scanned.

Figure 5A:
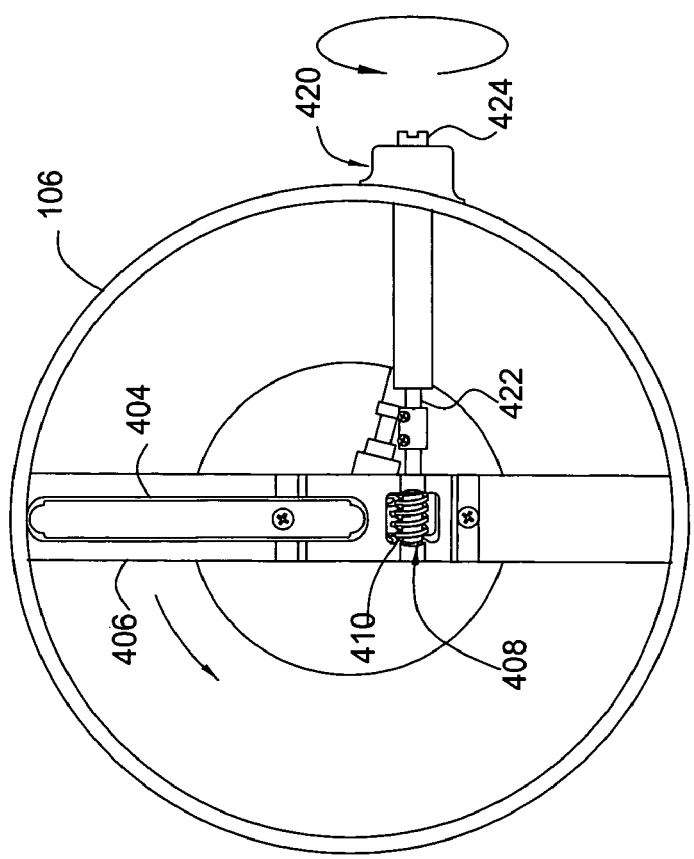
FIGS. 5A and 5B illustrate the movement of the probe in the scan housing of the filter system.
Figure 5B:
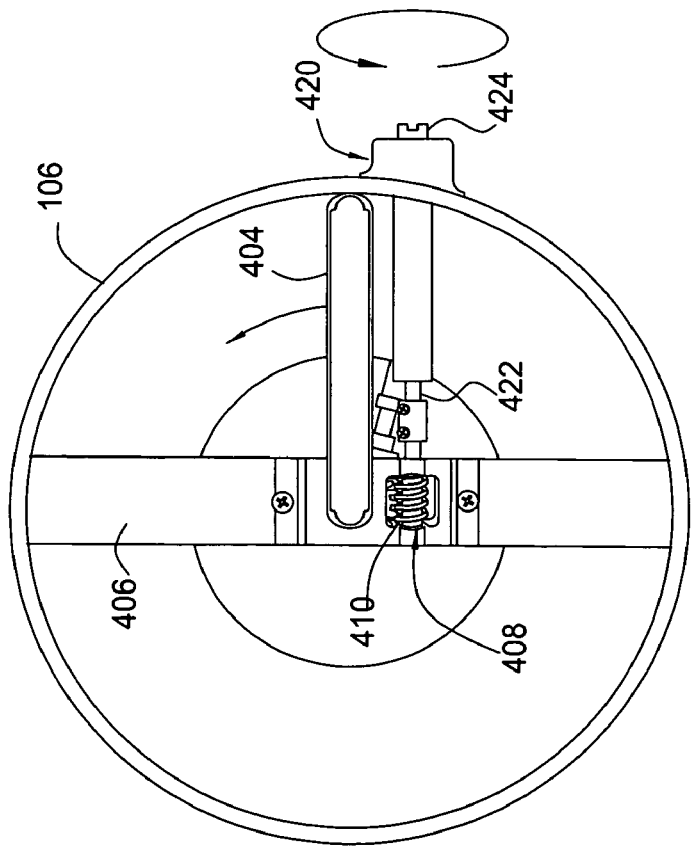

The actuator 408 may be any device suitable for moving the probe 402 within the scan test housing 104 without opening the pressure barrier of the system 100. In the embodiment depicted in FIG. 4, the actuator 408 is a gear mechanism 410. It is also contemplated that motors, rotary cables and other devices may alternatively be used to rotate the probe 402. In the embodiment depicted in FIGS. 5A–5B, the probe 402 is shown rotating about the centerline of the scan housing 106.

The gear mechanism 410 is utilized to provide rotary motion to the probe 402. A power transmission member, such as a shaft 422, is operably coupled to the gear mechanism 410 at one end and extends through a penetration 420 formed through the scan test housing 104 at a second end. The penetration 420 is sealed to the scan test housing 104. The penetration 420 includes a seal (not shown) that allows the shaft 422 to rotate without leakage from the system 100. In one embodiment, the seal 426 is a fluid seal, such as vacuum grease or other viscosity fluid or gel. It is contemplated that an elastomer seal may alternatively be utilized.

The end of the shaft 422 extending outside of the system 100 includes a head 424 that facilitates rotating the shaft. For example, the head 424 may include a flat, slot, key, hex or other drive feature to facilitate coupling a tool or motor to the shaft 422 so that rotational motion may be transmitted through the pressure barrier to the gear mechanism 410 so that the probe 402 may be rotated.

Figure 6:
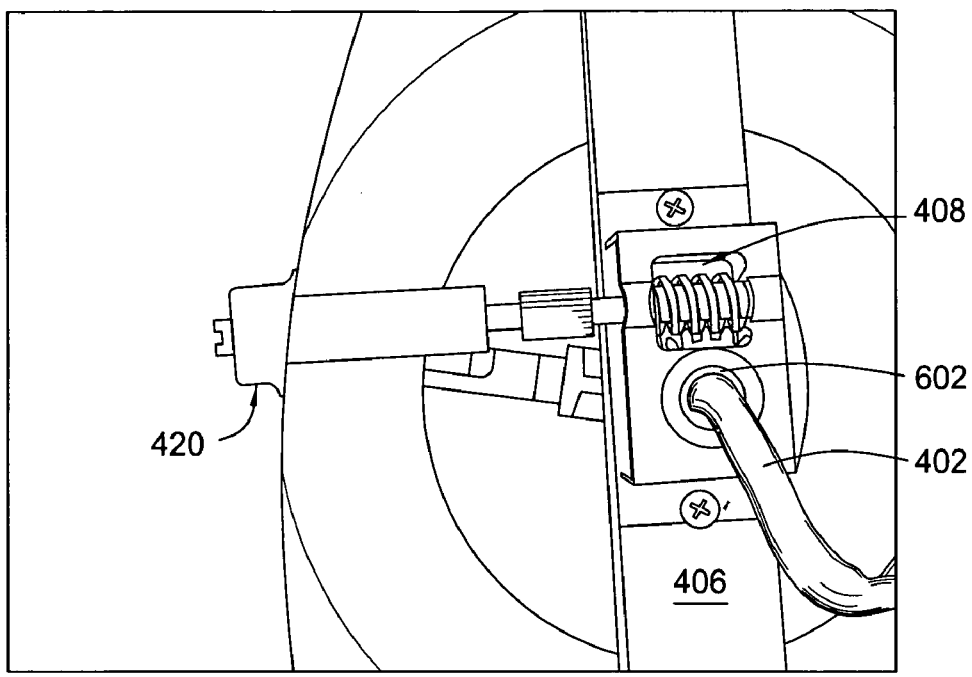
FIG. 6 depicts the gear assembly utilized to rotate the test probe.
Figure 7:
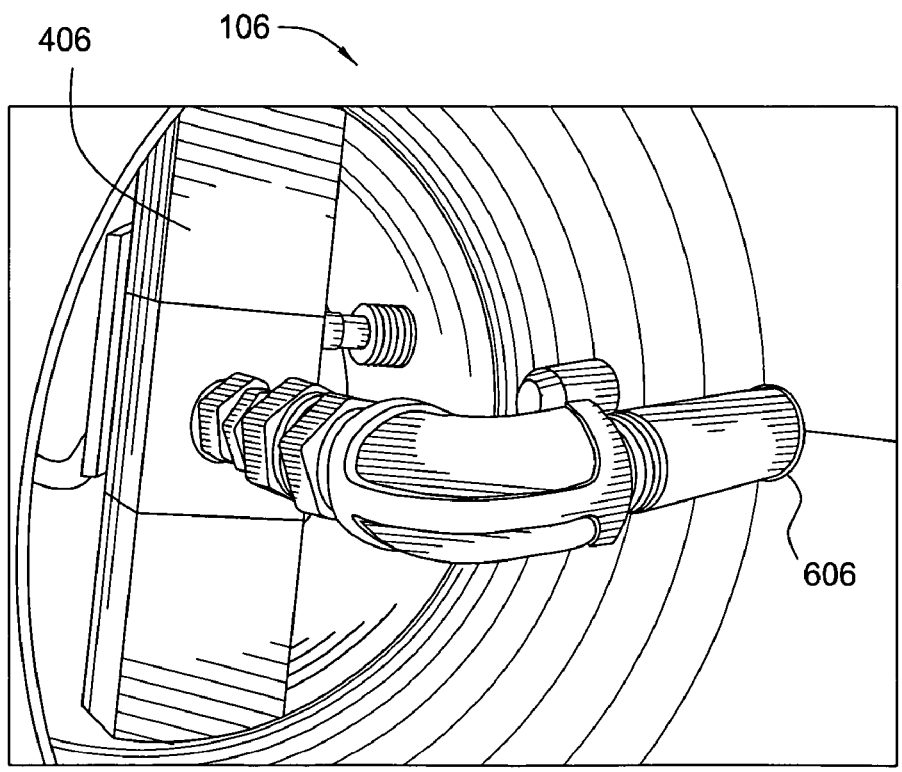
FIG. 7 is a bottom view of the gear assembly.
Figure 9:
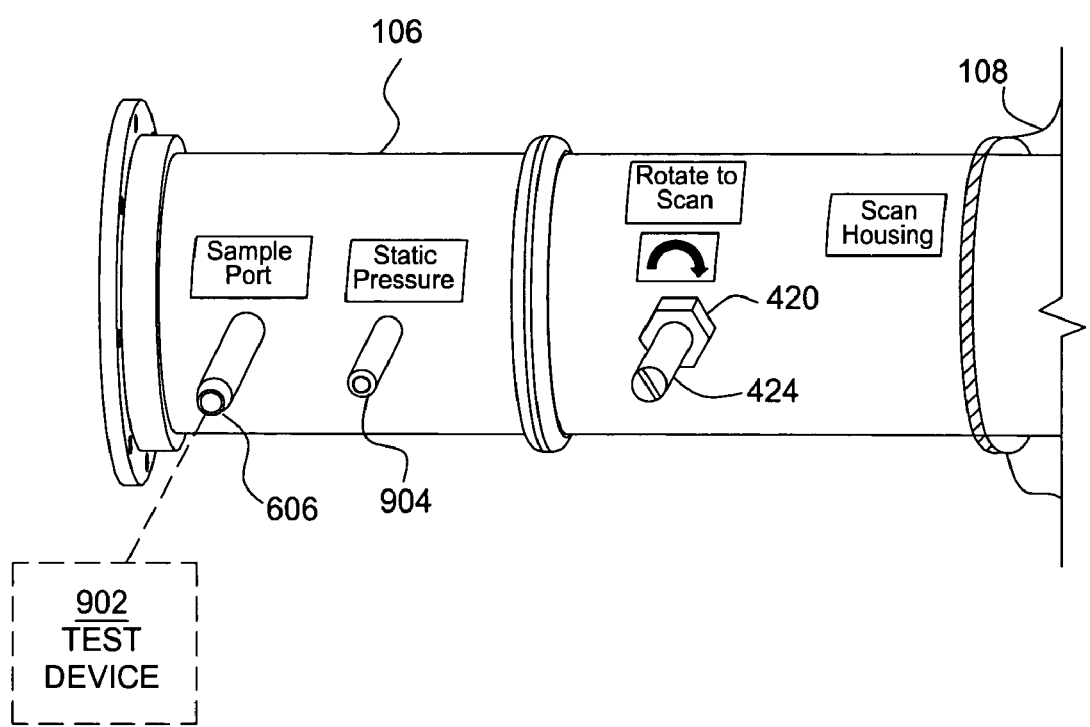

As shown in FIGS. 6–9, the penetration 420 for the operating mechanism of the actuator 408 and the sample port 606 of the probe 402 are sealed to the scan housing 106 to prevent leakage. FIG. 6 also depicts a leak-tight rotary union 602 that enables the probe 402 to rotate without contaminating the sample. The sample port 606 (e.g., that is fluidly coupled to the probe 402) may be coupled to a test device 902, for example, a flow meter, or an efficiency or leak testing device, such as a particle counter or potentiometer.

Figure 8:
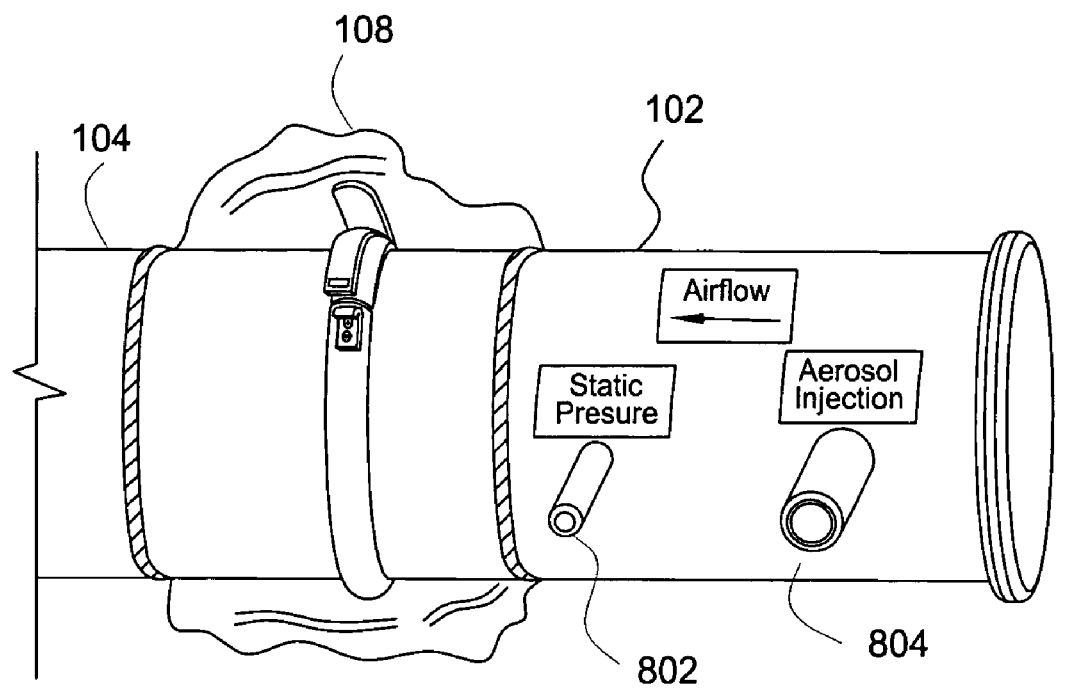

Thus, the system 100 enables a filter, installed in the filter housing 104, to be scan tested by rotating the probe 402 within the scan housing 106 downstream of the filter. As shown in FIG. 8, aerosol may be provide upstream of the filter through an aerosol injection port 804 formed in the upstream duct section 102. Both the upstream duct section 102 and the scan test section 106 may include static pressure ports (ports 802 904 are respectively shown in FIGS. 8–9). Added benefits include that as the probe 402 and mechanisms controlling the motion of the probe 402 are isolated with sealed penetrations from the environment outside the system, vacuum isolation of penetrations utilized to move probes in conventional systems is not required.

Additionally, the scan testable system 100 allowed the end user to have in-situ scan testing capabilities in accordance with the IEST-RP-CC-034.1 recommendations. The reduced size and compact form of this system 100 solves the space constraint issues that are generally encountered for not only retrofit applications, where the existing building or mechanical systems are undergoing renovation, but also for new construction, where there are efforts to reduce the size of mechanical systems in order to reduce the cost of the systems, as well as the capital costs of buildings and other associated equipment.

There are many possible configurations of the system, including:
  Bag-in/Bag-out (BIBO) configurations;
  Non-BIBO configurations;
  Decontamination ports;
  Manual scan capability, i.e., manually manipulated sample collection probe; and
  Autoscan capability, i.e., robotic (motor driven) sample collection probe.

There could also be combinations of any of the above systems. As an example: BIBO with decontamination ports and manual scan capability or Non-BIBO with no decontamination ports and manual scan capability.

Thus, a scan testable axial flow filter containment system has been provided that facilitates testing of the filter element without opening a pressure barrier of the containment system. Advantageously, the filter containment system allows leak detection, velocity measurements, efficiency testing to be performed with minimal disruption in operations as the testing may occur in-situ filter operation.

While the foregoing is directed to embodiments of the invention, other and further embodiments of the invention may be devised without departing from the basic scope thereof, and the scope thereof is determined by the claims that follow.

What is claimed is:

1. A filter system, comprising;
  an upstream duct housing;
  a filter housing coupled to the upstream duct housing;
  a scan test housing coupled to the filter housing;
  a probe suitable for leak testing disposed in the scan test housing; and
  a mechanism for moving the probe in a rotational motion tangentially to the inner edge of the filter housing that scans a filter disposed in the filter housing without opening the scan test housing.

2. The filter system of claim 1, wherein the mechanism for moving the probe further comprises:
  an actuator disposed in the scan test housing and coupled to the probe.

3. The filter system of claim 2, wherein the actuator is at least one of a motor, rotary cable or a gear mechanism.

4. The filter system of claim 1, wherein the mechanism for moving the probe spans from a center portion of the filter housing to an inner edge of the filter housing.

5. The filter system of claim 1, wherein the filter housing is cylindrical and has an axial flow path.

6. The filter system of claim 5, wherein the probe rotates relative to a centerline of the filter housing.

7. The filter system of claim 1, wherein the probe has a length of about one half of a diameter of the scan test housing in which the probe is disposed.

8. The filter system of claim 1, wherein the mechanism for moving the probe further comprises:
  a gear mechanism adapted to rotate the probe.

9. The filter system of claim 8, wherein the mechanism for moving the probe further comprises:
  a power transmission member coupled to the gear mechanism; and a penetration formed through the scan test housing adapted to facilitate selective rotation of the power transmission member from an exterior of the scan test housing without leakage from the system.

10. The filter system of claim 1 further comprising:
at least one bag-in/bag-out poly bag disposed adjacent the filter housing.

11. The filter system of claim 1, wherein the filter housing further comprises:
a filter element permanently sealed to the filter housing such that the filter housing, the scan test housing and the upstream duct housing form an exterior pressure boundary of the system.

12. A method for scanning a filter in a containment system, comprising:
flowing air through a filter;
rotating a probe tangentially to the inner edge of a filter housing to scan the filter; and
testing the filter using samples obtained while rotating the probe.

13. The method of claim 12, wherein the step of rotating the probe further comprises:
controlling the motion of the probe without opening a pressure boundary of the containment system.

14. The method of claim 13, wherein the step of controlling the motion of the probe further comprises:
rotating a shaft extending through a penetration formed through the pressure boundary.

15. The method of claim 12 further comprises:
prior to leak testing the filter, performing a bag-in, bag-out procedure comprising the steps of:
a) positioning a first bag over a filter housing having the filter sealingly coupled thereto, a first end of the first bag on a section of duct downstream of the filter housing and a second end of the first bag on a section of duct upstream of the filter housing;
b) releasing the filter housing disposed in the first bag from the upstream and downstream duct housings;
c) tying the first bag to isolate the filter housing and the upstream and downstream duct housings;
d) cutting the first bag to remove the isolated filter housing;
e) positioning a new filter housing having a filter sealingly coupled thereto between the upstream and downstream duct housings;
f) positioning a second bag over the new filter housing, a first end of the second bag on a section of duct downstream of the new filter housing and a second end of the second bag on a section of duct upstream of the new filter housing;
g) removing the first bag to expose the new filter housing to the upstream and downstream duct housings; and
h) sealing the new filter housing to the upstream and downstream duct housings.

16. The method of claim 12, wherein the step of testing further comprises:
detecting a filter leak, face velocity, or performing an efficiency test.

17. A filter system, comprising;
a scan test housing having a cylindrical inner passage and having a first end configured for coupling to a filter housing;
a sampling port formed through the scan test housing;
a probe suitable for leak testing disposed in the scan test housing in a radial orientation relative to a centerline of the passage, the probe fluidly coupled to the sampling port; and
a mechanism adapted to rotate the probe about the centerline while maintaining the probe in the radial orientation without opening the scan test housing.

18. The system of claim 17 further comprising:
a rotary union disposed within the housing and fluidly coupled to the sampling port and probe in a manner that facilitates probe rotation relative to the sampling port.

19. A method for scanning a filter in a containment system, comprising:
flowing air through a filter having a circular downstream face;
rotating a probe to scan the downstream face of the filter while maintaining a radial orientation of the probe relative to the downstream face of the filter; and
testing the filter using samples obtained while rotating the probe.

20. The method of claim 19, wherein the step of testing further comprises:
detecting a filter leak, face velocity or performing an efficiency test.

21. A filter system, comprising;
an upstream duct housing;
a filter housing coupled to the upstream duct housing;
a scan test housing coupled to the filter housing;
a probe suitable for leak testing disposed in the scan test housing; and
a mechanism for moving the probe in a rotational motion about a centerline of the filter housing while maintaining the probe in a radial orientation to the centerline that scans a filter disposed in the filter housing without opening the scan test housing.

* * * * *

UNITED STATES PATENT AND TRADEMARK OFFICE
CERTIFICATE OF CORRECTION

| | | |
|---|---|---|
| PATENT NO. | : 7,201,039 B2 | Page 1 of 1 |
| APPLICATION NO. | : 11/225812 | |
| DATED | : April 10, 2007 | |
| INVENTOR(S) | : Morse et al. | |

It is certified that error appears in the above-identified patent and that said Letters Patent is hereby corrected as shown below:

In column 3, line 31, after "the seal" delete "426".

In column 3, line 58, after "802" insert -- , --.

Signed and Sealed this

Nineteenth Day of June, 2007

JON W. DUDAS
*Director of the United States Patent and Trademark Office*